United States Patent
Huijbregtse et al.

(10) Patent No.: US 11,191,429 B2
(45) Date of Patent: Dec. 7, 2021

(54) DEVICE AND METHOD TO DETERMINE A STATE OF A LACRIMAL LAYER

(71) Applicant: Cassini Technologies B.V., 's-Gravenhage (NL)

(72) Inventors: Maarten Pieter Huijbregtse, 's-Gravenhage (NL); Haaije Rimmer De Vries, 's-Gravenhage (NL)

(73) Assignee: Cassini Technologies B.V., 's-Gravenhage (NL)

( * ) Notice: Subject to any disclaimer, the term of this patent is extended or adjusted under 35 U.S.C. 154(b) by 280 days.

(21) Appl. No.: 16/484,968

(22) PCT Filed: Feb. 23, 2018

(86) PCT No.: PCT/NL2018/050117
§ 371 (c)(1),
(2) Date: Aug. 9, 2019

(87) PCT Pub. No.: WO2018/156022
PCT Pub. Date: Aug. 30, 2018

(65) Prior Publication Data
US 2019/0357765 A1      Nov. 28, 2019

(30) Foreign Application Priority Data
Feb. 23, 2017 (NL) .................................... 2018411

(51) Int. Cl.
*A61B 3/10* (2006.01)
*A61B 3/00* (2006.01)
*A61B 3/14* (2006.01)

(52) U.S. Cl.
CPC ............ *A61B 3/101* (2013.01); *A61B 3/0008* (2013.01); *A61B 3/0025* (2013.01); *A61B 3/14* (2013.01)

(58) Field of Classification Search
CPC ..... A61B 3/101; A61B 3/0008; A61B 3/0025; A61B 3/14
USPC ......................................................... 351/206
See application file for complete search history.

(56) References Cited

U.S. PATENT DOCUMENTS

2013/0308100 A1    11/2013   Mensink

FOREIGN PATENT DOCUMENTS

| EP | 1 844 702 A1 | 10/2007 |
|----|--------------|---------|
| JP | 2006-204773 A | 8/2006 |
| WO | 2012/067508 A1 | 5/2012 |
| WO | 2016/067332 A1 | 5/2016 |

*Primary Examiner* — Mohammed A Hasan
(74) *Attorney, Agent, or Firm* — Hoffmann & Baron, LLP (57) ABSTRACT

A device to determine a state of the lacrimal layer of the eye includes at least one light source arranged to form a pattern of source points for projecting a plurality of light rays onto a cornea surface; a lens-camera system arranged to receive a respective plurality of reflected light rays reflected on the cornea surface, thereby forming a pattern of image points; and a computational unit arranged to determine on the basis of the image points the state of the lacrimal layer of the eye and/or to determine on the basis of the image points data representative for the state of the lacrimal layer of the eye and to provide the data representative for the state of the lacrimal layer of the eye to a user.

20 Claims, 5 Drawing Sheets

DEVICE AND METHOD TO DETERMINE A STATE OF A LACRIMAL LAYER

CROSS-REFERENCE TO RELATED APPLICATIONS

This application is the National Stage of International Application No. PCT/NL2018/050117, filed Feb. 23, 2018, which claims the benefit of Netherlands Application No. 2018411, filed Feb. 23, 2017, the contents of which is incorporated by reference herein.

FIELD OF THE INVENTION

The invention relates to a device to determine a state of a lacrimal layer of an eye. The invention further relates to a method to determine a state of a lacrimal layer of an eye.

BACKGROUND OF THE INVENTION

The cornea surface of an eye is normally covered with a lacrimal layer, i.e. a layer of lacrimal fluid on the cornea surface. This lacrimal layer is also known as tear film or tear film layer. Due to evaporation of the lacrimal fluid, the lacrimal layer gradually becomes thinner during the time the eyelid remains open after blinking. After a period of time the lacrimal layer will even break up, but normally, a person will blink before breakup of the lacrimal layer. The movement of the eyelid over the cornea surface will restore the lacrimal layer.

In the prior art, several devices have been proposed to monitor the state of the lacrimal layer, in particular to determine the break up time (TBUT) of a lacrimal layer. The time period between a blink of an eye and subsequent breakup of the lacrimal layer provides information on the quality of the lacrimal layer formed during the blink of the eye.

EP 1 844 702 discloses a device configured to non-invasively measure the state of the lacrimal layer formed on the cornea surface. The device of EP 1 844 702 comprises an optical projection system to project a ring shaped pattern comprising multiple concentric rings onto the cornea surface. An imaging device, for example a CCD camera, is provided to receive a reflection image of the projected light from the cornea surface. An operating unit calculates the degree of distortion of the reflection image on the basis of the density value distribution of the image photographed by the imaging device. On the basis of the calculated degree of distortion, the operating unit can quantify the state of the lacrimal layer.

Although the device of EP 1 844 702 provides a device that can noninvasively measure the state of the lacrimal layer formed on the cornea surface and that can quantitatively measure the state of the lacrimal layer without utilizing a reflection image from the retina, the results of the device are still limited.

SUMMARY OF THE INVENTION

It is therefore an object of the invention to provide a device and/or method to determine a state of the lacrimal layer, that is capable of providing improved results with respect to the determination of the state of the lacrimal layer, or at least to provide an alternative device and/or method, respectively.

The invention provides a device to determine a state of the lacrimal layer of the eye, comprising:

at least one light source arranged to form a pattern of source points for projecting a plurality of light rays onto a cornea surface;

a lens-camera system arranged to receive a respective plurality of reflected light rays reflected on the cornea surface, thereby forming a pattern of image points; and a computational unit arranged to determine on the basis of the image points the state of the lacrimal layer of the eye and/or to determine on the basis of the image points data representative for the state of the lacrimal layer of the eye and to provide the data representative for the state of the lacrimal layer of the eye to a user.

The device of the invention provides a pattern of source points for projecting a plurality of light rays onto a cornea surface and a pattern of image points that is formed by a respective plurality of reflected light rays reflected on the cornea surface.

It has been found that the image points may provide a good basis to determine the state of the lacrimal layer of the eye, as the image points may provide more useful distortion information than for instance a pattern of rings as proposed in EP 1 844 702. For example, points have a more precise local definition. Local deformations in all directions may be recognized, while ring-shaped patterns can only be used detect radial directed deformations. Furthermore, in a ring shaped pattern it may be more difficult to distinguish between local and global distortion of a projected pattern.

As a result of the use of a pattern of image points, the determination of the state of the lacrimal layer may be based on only a few images, i.e. less than five images. Preferably, the determination is based on a single image.

The computational unit may be arranged to determine on the basis of the image points the state of the lacrimal layer of the eye. The computational unit may for example be configured to calculate a value representative for the present state of the lacrimal layer at a certain location or region in the eye and indicate whether this value exceeds one or more threshold values.

It is also possible that the computational unit is arranged to determine on the basis of the image points data representative for the state of the lacrimal layer of the eye and to provide the data representative for the state of the lacrimal layer of the eye to a user, e.g. an operator of the device, a physician or any other person interested in this data. This data representative for the state of the lacrimal layer enables the user to determine, preferably directly determine, the state of the lacrimal layer of the eye.

Since the device of the invention enables the user to obtain or determine the state of the lacrimal layer of an eye, or at least data representative for the state of the lacrimal layer of the eye, this information may also be used for diagnosis of ocular surface disorders, such as dry eye syndrome. Further, since the state of the lacrimal layer can be determined with only a few images, and therefore within a small time interval, the device of the invention can also be used to monitor the development of the lacrimal layer in the course of time. For example, the break up time of a lacrimal layer may be determined.

It is remarked, that, in an embodiment, each source point may have its own light source, for example a LED may be provided for each source point. In this embodiment the device will have a plurality of light sources. As an alternative, all source points of sub-groups of source points can be linked to a single light source, for example a light source of which light is distributed over multiple optical fibers, the end-points of the optical fiber forming source points to emit rays of light towards the corneal surface.

In an embodiment, the computational unit is arranged to determine the state of the lacrimal layer of the eye on the basis comparing the source points and the image points and/or comparing the pattern of the source points and the pattern of the image points. Comparison of the source points and the image points, or their patterns, can be used to determine the state of the lacrimal layer. A regular consistent lacrimal layer with sufficient thickness will have a mirror like reflection. As a result, the image point and the source point will have similar shapes and/or dimensions. When the state of the lacrimal layer diminishes, for example in the case of an irregular lacrimal layer or a relatively thin lacrimal layer, the image points and/or their pattern formed from the reflected light rays will be more distorted.

In an embodiment, the computational unit is configured to determine for each of multiple image points, a value representative for local distortion of the respective image point, wherein the value representative for local distortion of the respective image point can be used to determine the state of the lacrimal layer of the eye.

Local distortion is herein defined as a degree in which an individual source point is imperfectly reflected and received as an image point due to a local cause. This imperfect reflection is typically caused by a local state of the lacrimal layer, i.e. independent of the state of the lacrimal layer at other locations. Since the imperfect reflection is caused by a local state of the lacrimal layer, the shape and intensity of reflection will typically be different for different image points, even if the state of the lacrimal layer associated with these image points is substantially the same.

A value representative for local distortion of the respective image point, also indicated herein as local distortion factor, provides a value that is representative for the local state of the lacrimal layer since only locally caused imperfect reflections are taken into account.

In an embodiment, the computational unit may, for example, be arranged to establish the value representative for local distortion by the following steps:

defining regions around a central position of each image point, wherein the defined regions are non-overlapping and preferably adjacent;

analyzing the shape of each individual image point within its defined region; and quantifying the value representative for local distortion of the respective image point for each individual image point based on the analyzed shape.

This quantification may for example be 0 for focused points and 1 for locally distorted points, but also a more distributed scale, for example a range of 1-5 or a range of 1-10 may be used to quantify the local distortion of an individual image point into a local distortion factor.

The distribution of the defined regions and the associated local distortion factor may be displayed in a map, for example by using colour codes/scales to indicate the amount of local distortion within a certain region.

In an embodiment, the computational unit is arranged to determine a pattern of grid lines, wherein cross-points of the grid lines are formed by determined locations of the image points, and wherein the state of the lacrimal layer of the eye, or data representative thereof, can be determined by a distortion within the pattern of grid lines. To determine this pattern of grid lines, the computational unit may first calculate the location of the image points, for example by calculating a center point of each image point of the pattern of image points. These center points can be connected to each other by connecting lines to form grid lines.

The pattern of source points may for example be selected such that most grid lines are either parallel or perpendicular with respect to each other. As a result, when the pattern of grid lines shows many straight and parallel or perpendicular grid lines, it can be concluded that the state of the lacrimal layer is relatively good, and when the pattern of grid lines shows many non-straight and unparalleled or non-perpendicular grid lines, it can be concluded that the state of the lacrimal layer is relatively bad.

The pattern of grid lines may be presented to a user to enable the user to determine on the basis of the data the state of the lacrimal layer of the eye.

In another embodiment, the computational unit may be arranged to determine on the basis of the grid line representation the state of the lacrimal layer of the eye by analyzing the straightness of the grid lines and the parallelism or perpendicularity of the grid lines with respect to each other.

In an embodiment, the device comprises a display device arranged to display the state of the lacrimal layer of the eye and/or the data representative for the state of the lacrimal layer of the eye. The display device may be a computer screen, but also a printer. It is advantageous that relevant data, such as graphical information can be presented to the user. The display device may for example be arranged to display a pattern of grid lines that represents the state of the lacrimal layer of the eye.

In an embodiment, the computational unit comprises a memory unit provided with pattern information based on the pattern of source points, wherein the computational unit is arranged to, for each of the plurality of reflected light rays, establish a one-to-one correspondence between a source point and an image point based on the pattern information, wherein the computational unit further is arranged to determine on the basis of a comparison of the image points and the source points the state of the lacrimal layer of the eye.

The data results of the comparison of source and image points may for example be stored in a database, and compared with previously obtained data of the same eye or with reference data, for example obtained from the other eye of the same person or from other persons. The data may also be used over a longer period of time, for example to determine the effects of treatment of ocular surface disorders, such as dry eye syndrome.

In an embodiment, the computational unit is arranged to determine the state of the lacrimal layer of the eye on the basis of individual comparisons of an image point of the pattern of image points and a corresponding source point of the pattern of source points.

The computational unit is arranged to, for each of the plurality of reflected light rays, establish a one-to-one correspondence between a source point and an image point based on the pattern information of the pattern of source points. This enables the computational unit to make a one-to-one comparison between a source point and an image point, and to determine for each of the image points a quantitative evaluation of the state of the lacrimal layer at the location on the cornea surface corresponding to that respective image point. It will be clear that in particular the use of patterns of source points and image points provides the possibility make a proper individual comparison between a source point and a corresponding image point.

After the individual comparison of source points and corresponding image points, the results of the individual comparisons may be grouped in order to provide a single qualitative value for one or more areas of the ocular surface or a single qualitative value representative for the state of the lacrimal layer of the complete cornea surface of the respective eye.

The results of the comparison, i.e. the state of the lacrimal layer may for example be presented in a map. In the map values associated with individual source and image points or associated with selected groups of source and image points may be presented. The map may for instance be shown in a computer display or printed on paper.

In an embodiment, the computational unit is arranged to determine a value representative for global distortion of an image point, wherein the value representative for global distortion of the respective image point is representative for effects of a global cause that affects a large number, possible all image points, in substantially the same way and wherein the computational unit is arranged, when desired, to correct or compensate an individual image point for the effects of the global cause using the value representative for global distortion of the image point.

Global distortion is herein defined as a degree in which a complete pattern of source points is imperfectly reflected and received as a pattern of image points due to a global cause. This imperfect reflection is for example caused by movement of the device with respect to the lacrimal layer. Since the imperfect reflection is caused by a global cause, the change in shape and/or intensity of reflection will typically be substantially the same for all image points.

Since global distortion of the image points results from a global cause, typically movement of the device with respect to the lacrimal layer during the period of projecting the plurality of light rays onto the cornea surface and receiving the respective plurality of reflected light rays reflected on the cornea surface. When the global distortion effects are not taken into account during processing of the image data, in particular during comparison of an individual source point and a corresponding image point, the effects caused by global distortion may have negative effect on the assessment of the state of the lacrimal layer.

Therefore, the computational unit may be arranged to correct an individual image point for the effects of the movement. It may be possible that the computational unit first establishes whether substantial global distortion is present in the pattern of image points, and only will correct/compensate the pattern of image points when it is established that substantial global distortion has been taken place.

In an alternative embodiment, the device may be configured to determine that the pattern of image points is not suitable to determine the state of the lacrimal layer of the eye, when the value representative for global distortion exceeds a predetermined threshold value.

The global distortion of the image points will typically be determined by searching for the same distortion in a substantial number of image points, preferably all image points. By quantifying these corresponding distortions a value representative for global distortion can be established. This value representative for global distortion, herein also indicated as the global distortion factor or stability quality factor, can be used to correct and/or compensate the individual image points.

In an embodiment, the pattern information comprises an identifier for each of the source points. In order to determine a one-to-one correspondence between the source points and the image points, an identifier may be used for each point.

In an embodiment, wherein the at least one light source comprises light sources that project light rays with different colours such that the pattern of source points comprises at least two different colors. By using different colours in the pattern of source points, the effort with which the one-to-one correspondence between the source points and the image points can be established can be substantially decreased, and/or the reliability with which the one-to-one correspondence between the source points and the image points can be established can be substantially increased. In order to obtain a proper evaluation and comparison of the source points and the image points, it is of high importance that the matching of source points and image points is performed accurately.

The invention further provides a method of determining a state of the lacrimal layer of an eye, the method comprising:

projecting, with at least one light source, a plurality of light rays from a pattern of source points onto a cornea surface;

receiving, a lens-camera system, a respective plurality of reflected light rays reflected on the cornea surface thereby forming a pattern of image points; and determining, with a computational unit, the state of the lacrimal layer of the eye on the basis of the image points and/or determining, with a computational unit, on the basis of the image points data representative for the state of the lacrimal layer of the eye and providing the data representative for the state of the lacrimal layer of the eye to a user.

In an embodiment, the step of determining the state of the lacrimal layer of the eye comprises comparing the source points and the image points and/or comparing the pattern of the source points and the pattern of the image points.

In an embodiment, the step of determining the state of the lacrimal layer of the eye comprises determining for each of multiple image points a value representative for local distortion of the respective image point wherein the value representative for local distortion of the respective image point can be used to determine the state of the lacrimal layer of the eye.

In an embodiment, the step of determining the value representative for local distortion comprises:

defining regions around a central position of each image point, wherein the defined regions are non-overlapping and preferably adjacent;

analyzing the shape of each individual image point within its defined region; and quantifying a value of the local distortion factor for each individual image point based on the analyzed shape.

In an embodiment, the method comprises the step of determining a pattern of grid lines, wherein cross-points of the grid lines are formed by determined locations of the image points, and wherein a distortion within the pattern of grid lines is representative for the state of the lacrimal layer of the eye.

In an embodiment, the method comprises displaying, with a display device, the state of the lacrimal layer of the eye and/or the data representative for the state of the lacrimal layer of the eye.

In an embodiment, the method comprises the steps of creating a map showing the local distortion of the respective image points or groups of image points.

In an embodiment, the method comprises:

providing pattern information based on the pattern of source points;

establishing a one-to-one correspondence between each of the source points and the respective image points based on the pattern information; and comparing the image points and the source points to determine the state of the lacrimal layer of the eye.

In an embodiment, the step of comparing comprises determining the state of the lacrimal layer of the eye on the basis of individual comparisons of an image point of the pattern of image points and a corresponding source point of the pattern of source points.

In an embodiment, the method comprises the steps of:

determining a value representative for global distortion of an image point, wherein the value representative for global distortion of the respective image point is representative for effects of a global cause that affects a large number, possibly all image points, in substantially the same way, and correcting or compensating an individual image point for the effects of the global cause using the value representative for global distortion of the image point, and/or when the value representative for global distortion exceeds a predetermined threshold value determining that the pattern of image points is not suitable to determine the state of the lacrimal layer of the eye.

BRIEF DESCRIPTION OF THE DRAWINGS

An embodiment of a device according to the invention will now be described in further detail, by way of example only, with reference to the accompanying drawings, in which.

DETAILED DESCRIPTION OF THE INVENTION

Figure 1:
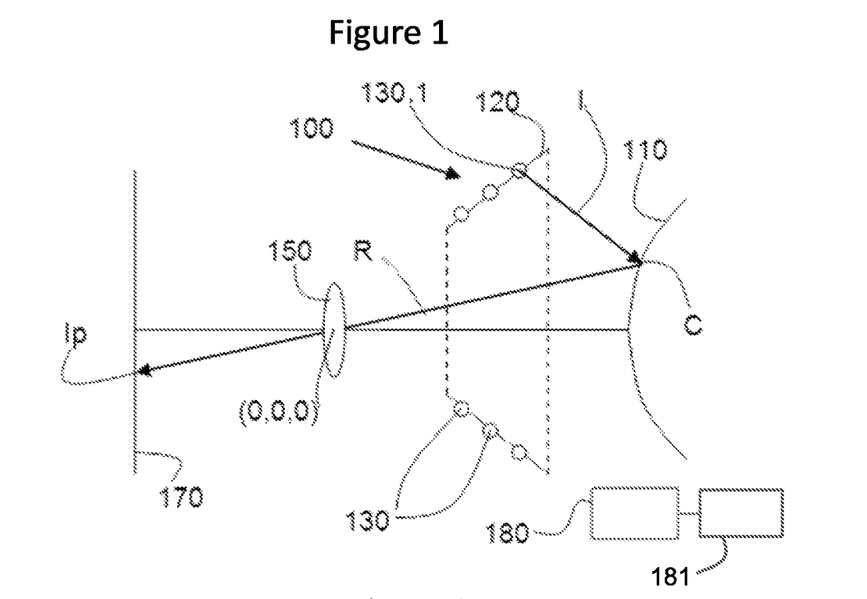
FIG. 1 shows an embodiment of a device according to the invention.

In FIG. 1, an embodiment of a device according to the present invention is schematically shown. This device is configured to determine a state of a lacrimal layer of an eye.

The device is based on a corneal topographer as shown and described in WO 2012/067508, the contents of which are herein incorporated by reference in its entirety.

The embodiment of FIG. 1 schematically shows a multicolored stimulator 100 arranged to project a plurality of light rays onto a corneal surface 110. The stimulator 100 may e.g. have a conical shaped or a hemispherical shaped surface 120 whereby a plurality of the source points is arranged on this surface 120 for projecting the plurality of light rays onto the corneal surface 110. In an embodiment, the source points can be provided by mounting LEDs 130 of different color onto the surface 120. As an alternative, the source points can be formed by end-points of fiber optics arranged to emit rays of light towards the corneal surface 110.

As schematically shown, an incident ray of light I, emitted by source point (Sp) 130.1 (having coordinates (Xs, Ys, Zs)) intersects the corneal surface 110 (at corneal intersection point C (having coordinates (Xc, Yc, Zc)) and results in a reflected ray of light R towards a lens 150 of a lens-camera system for recording the corneal reflection. The reflected ray of light R is subsequently received by a camera plane 170 of the lens-camera system resulting in an image point (Ip) having coordinates (Xi, Yi, Zi). As can be seen from FIG. 1, the opening of the cone 120 (or hemisphere) faces the corneal surface 110 of the eye to be measured. The device as shown further comprises a computational unit 180, e.g. a computer, or microprocessor for processing the captured images and construct, based on the captured image, a mathematical representation of the state of the lacrimal layer. The computational unit 180 comprises a memory unit to store relevant data, such as pattern information of the source points. A display device 181, for example a computer screen or printer may be provided to display relevant data.

Figure 2:
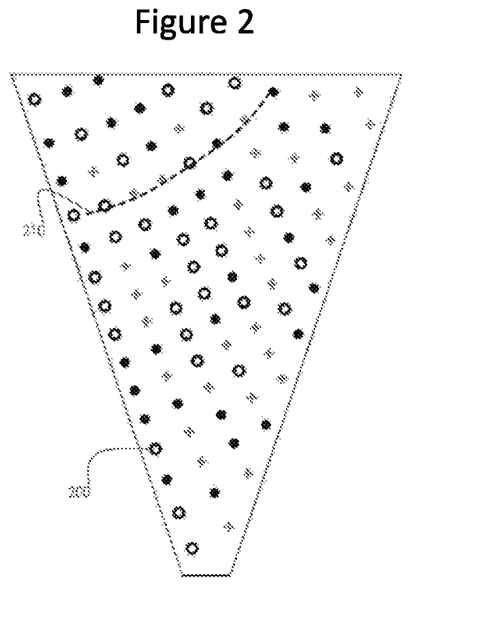
FIG. 2 schematically shows a panel comprising a multicolored source point pattern as can be applied in a topographer according to the invention.
Figure 3:
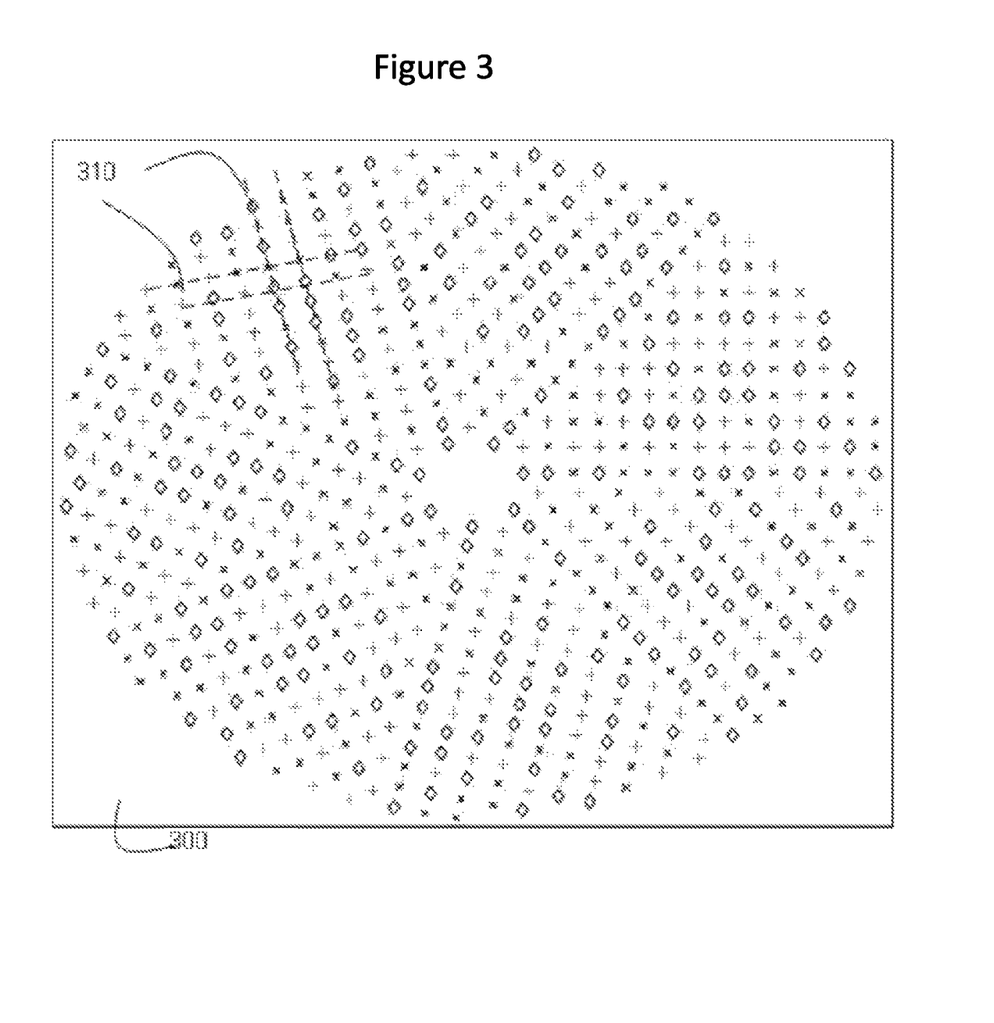
FIG. 3 schematically shows an image point pattern as obtained using a stimulator comprising 7 panels as shown in FIG. 2.

In an embodiment, the multicolored stimulator comprises a plurality of segments, which can be identical or not. As an example of such embodiment, the source points of the stimulator are mounted to a plurality of boards such as PCBs. In such an arrangement, multiple PCB panels can be assembled to form a substantially conic shape. As an example, such a stimulator can be constructed using at least 3 panels. Below, a more detailed example is shown comprising 7 PCB panels. FIG. 2 schematically shows a plan view of such a panel 200 whereby the symbols o, + and • are used to denote source point positions of different color. In the example shown, 96 source points (e.g. LEDs) are arranged on the panel. 7 of such panels, whereby each PCB panel can have an identical arrangement of source points, i.e. colored LEDs, can be assembled to form the substantially conical stimulator. In an embodiment, the arrangement of source points on a panel is such that a reflection on a spherical surface will form a substantially rectangular grid pattern. In FIG. 3, the resulting image pattern 300 when 7 panels according to FIG. 2 are used, is schematically shown. As indicated by the dotted lines 310, the image points obtained from a substantially rectangular grid pattern. In order to identify a particular panel from the other panels (assuming the panels to be identical), the orientation of the rectangular grid pattern can be used. Such an orientation can thus be used to help establishing a unique identification of an image point. The orientation of the grid pattern can e.g. be derived from assessing the positions of a subset of image points. As can be seen from the source point pattern in FIG. 2, in order to realize such a rectangular grid pattern as an image point pattern, the source points can be arranged along curved lines, e.g. curvature 210 as indicated in FIG. 2.

In order to establish a one-to-one correspondence between the source points and the image points, the device applies color pattern information based on the multicoloured pattern of source points. Such information can e.g. describe parts of the color pattern, e.g. as a plurality of arrays of matrices. As an example, n×m matrices (e.g. 2×2 or 3×3) can be used to describe the color pattern of n×m source points. By matching the color patterns of the matrices to the pattern of the image points, a correspondence between the image points and the source point can be established.

As described above, the device of the invention comprises at least one light source arranged to form a pattern of source points for projecting a plurality of light rays onto a cornea surface of an eye to be examined and a lens-camera system arranged to receive a respective plurality of reflected light rays reflected on the cornea surface, thereby forming a pattern of image points.

After the computational unit 180 has received the pattern of image points, the computational unit 180 will establish, for each of the plurality of reflected light rays, a one-to-one correspondence between a source point and an image point based on the pattern information, that is stored in the memory unit.

The computational unit 180 may then determine on the basis of a comparison of the image points and the source points the state of the lacrimal layer of the eye. The comparison is based on individual comparisons of an image point of the pattern of image points and a corresponding source point of the pattern of source points. This approach is based on the insight that the reflectiveness of a cornea surface at a certain location on the cornea surface depends on the state of the lacrimal layer of the cornea surface at that location. In particular, a value representative for the local distortion of the image point with respect to the source point is a reliable measure in determining the state of the lacrimal layer.

Local distortion is the degree in which an individual source point is imperfectly reflected and received as an image point. This imperfect reflection is typically caused by a local state of the lacrimal layer, i.e. independent of the state of the lacrimal layer at other locations. Since the imperfect reflection is caused by a local state of the lacrimal layer, the shape and intensity of reflection will typically be different for different image points even when the state of the lacrimal layers at the locations of the different image points is substantially the same. It is remarked that local distortion in the reflection of a single source point may result in a change in shape or dimension. Also, a single source point may be distorted in such way that the image point breaks up in multiple spots.

The source points will be small light spots resulting from the plurality of light rays projected on the cornea surface. These source points have for example a circular shape with relative small diameter. In dependence of the reflectivity of the cornea surface at the location where the image point is projected on the cornea surface, the reflection will be more mirror like when the state of the lacrimal layer is relatively good, and more locally distorted when the state of the lacrimal layer is relatively bad.

However, another effect may also have an influence on the reflection of the light rays on the cornea surface. This effect is called global distortion. Global distortion is herein defined as a degree in which a complete pattern of source points is imperfectly reflected and received as a pattern of image points. This imperfect reflection of the complete pattern is caused by a global cause, for example a movement of the device with respect to the cornea surface. Since the imperfect reflection is caused by a global cause, the effect on change in shape and intensity of reflection will typically be substantially the same for different image points in the pattern of image points.

In order to accurately use the source points and the image points to determine a state of the lacrimal layer of the eye, the effects of global distortion, if present, should be corrected or compensated. It may be possible that the computational unit 180 first establishes whether the global distortion factor exceeds a certain threshold value, and only will correct/compensate when the global distortion exceeds this threshold value. It may also be decided that, due to global distortion, the pattern of image points is not suitable for determining the state of the lacrimal layer when the global distortion factor exceeds a certain threshold value.

Figure 4:
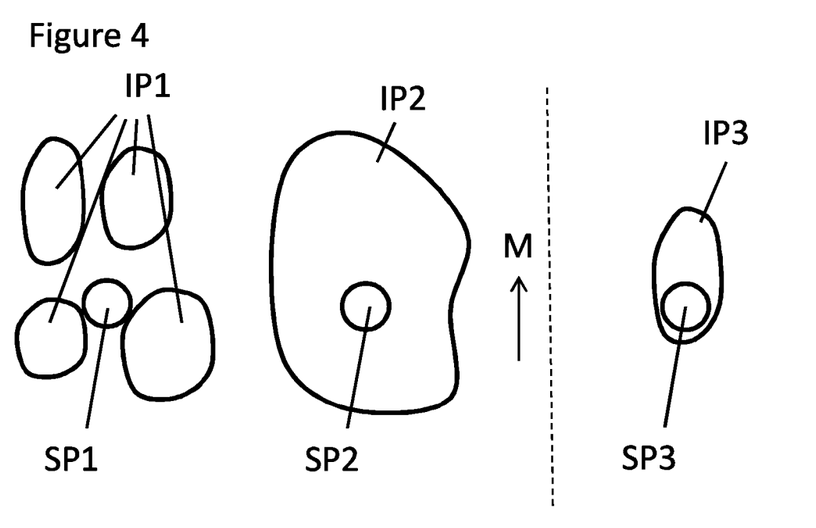
FIGS. 4 and 5 each show schematically three source points and associated image points.

FIG. 4 shows, as an example, three source points SP1, SP2, SP3 and three image points IP1, IP2, IP3. It is remarked that, due to local distortion, the first image point IP1 comprises multiple (four) image spots. The computational unit 180 has already established a one-to-one correspondence between the source points SP1, SP2, SP3 and the corresponding image points IP1, IP2 and IP3, respectively. It is remarked that the first and second source points SP1, SP2 and the first and second image points IP1, IP2 are located relatively close to each other compared to the location of the third source point SP3 and the third image point IP3. This is indicated in FIG. 4 by a dashed separation line.

In FIG. 4, the source points and image points are depicted on top of each other. By evaluating of the pattern of source points SP1, SP2, SP3 and the associated pattern of image points IP1, IP2, IP3, it can be established that all the image points comprise a corresponding distortion that is caused by movement of the device with respect to the cornea surface during projection of the light rays and receipt of the reflected light rays. This movement is indicated with an arrow M. Since these corresponding distortions in the pattern of image points are caused by a global cause, it is desirable to correct/compensate these distortions, such that these distortions are not used as an indicator for the state of the lacrimal layer. This compensation can be carried out by determining a global distortion factor, a corresponding distortion in substantially all image points, and using this global distortion factor to compensate the distortion for the whole pattern of image points.

Figure 5:
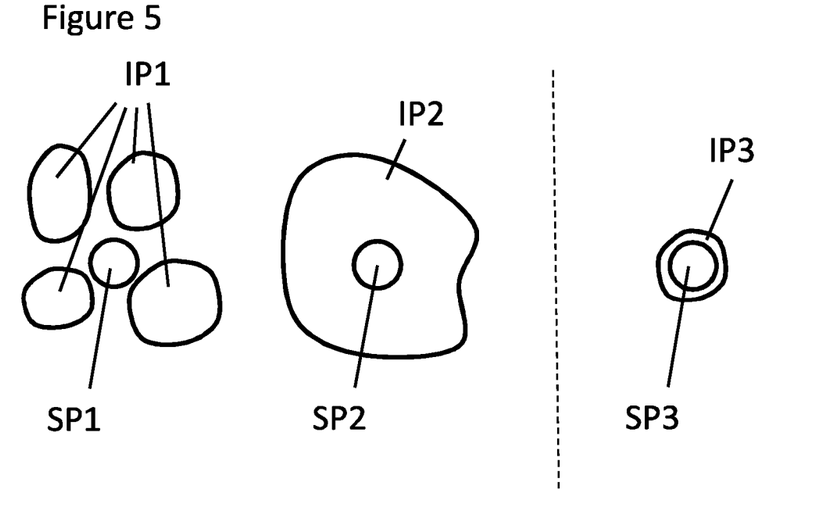

FIG. 5 shows three source points SP1, SP2, SP3 and three image points IP1, IP2, IP3 after such compensation. It is remarked that the compensation may also be carried out in any other suitable way, and does not necessarily have to result in a shape change of the respective image points IP1, IP2, IP3.

Now, it can be seen that the first and second image point IP1, IP2 show a relatively locally distorted shape compared with the corresponding source point SP1, SP2, respectively. In contrast, the shape of the third image point IP3 is only slightly changed with respect to the third source point SP 3. It can be concluded that at the location on the cornea surface associated with the third image point IP3 a relatively good mirror like reflection is obtained, indicating a good state of the lacrimal layer, while at the location of the cornea surface of the first and second image point IP1, IP2, a poor reflection, with relative high local distortion is obtained indicating a poor state of the lacrimal layer.

In order to provide useful feedback on the local distortion of each of the image points, the computational unit 180 is arranged to determine for each of multiple image points, a value representative for local distortion of the respective image point, wherein the value representative for local distortion of the respective image point can be used to indicate/determine the state of the lacrimal layer of the eye.

In an embodiment, the following steps are performed to establish the value representative for local distortion of a respective image point.

Figure 6:
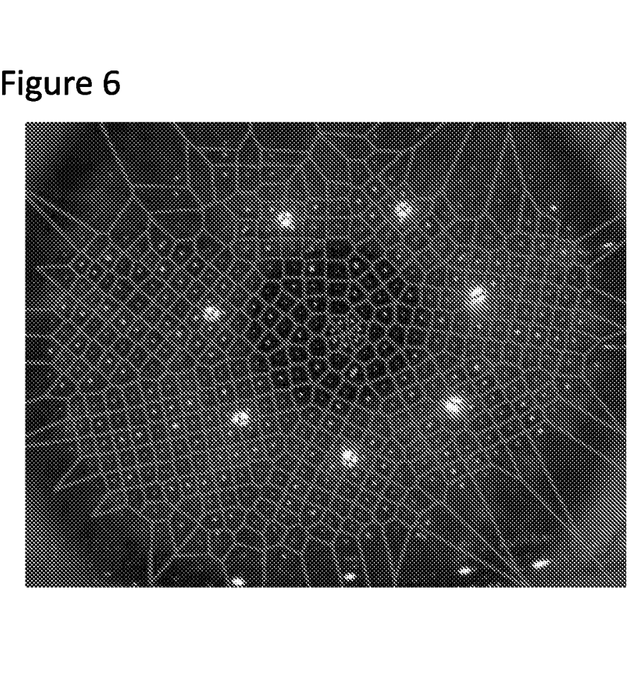
FIG. 6 shows a mosaic of defined regions, whereby each region is associated with a single image point.

As a first step the computational unit 180 defines, for each image point a region around a central position of that image point, wherein the defined regions are non-overlapping and adjacent. An example of such mosaic of regions is shown in FIG. 6.

In a next step, the shape of each individual image point within its own defined region may be examined by the computational unit 180, and thereafter the local distortion factor, i.e. a value representative for local distortion of the respective image point, may be quantified for each individual image point based on the analyzed shape.

Quantification of the local distortion within each region may be performed with any suitable scoring system. For example, the image points may be classified in two categories, locally non-distorted or locally distorted. The locally non-distorted regions may for example be indicated with '0' and the locally distorted regions may be indicated by '1'. The scoring system may also comprise multiple scales, such as non-distorted, low distorted, medium distorted, high distorted, and very high distorted, for example indicated by a scale from '1' tot '5'. Any other scoring system may also be applied.

To express the state of the lacrimal layer, the smudge factors for individual image points may also be combined to a combined local distortion factor for certain areas of the eye. For example, for each panel of the stimulator, (one panel shown in FIG. 2), a combined local distortion factor may be determined with which the state of the lacrimal layer for the respective area of the cornea surface is indicated. It is also possible that one single local distortion factor is determined for the whole cornea surface of the eye.

Figure 7:
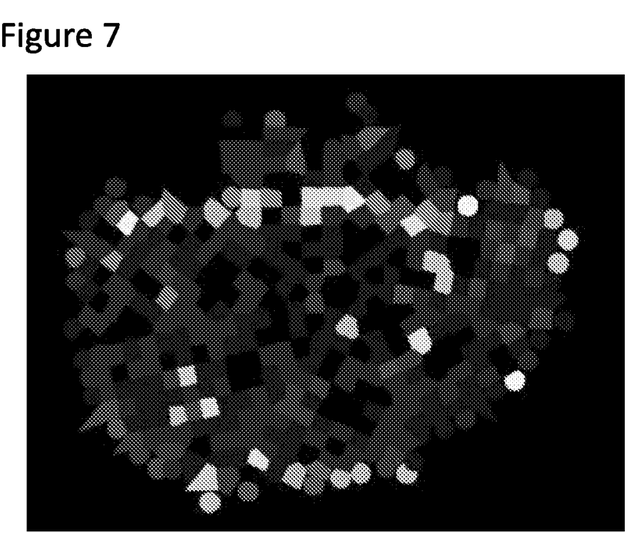
FIG. 7 shows a map indicating for each individual region a state of the lacrimal layer of the eye.
Figure 8:
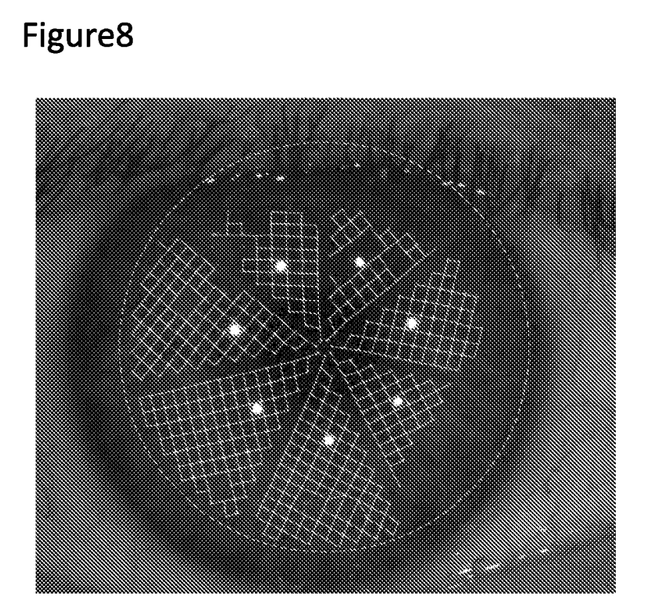
FIGS. 8 and 9 show an example of a grid lines presentation representative for the state of the lacrimal layer of the eye.

FIG. 7 shows a map in which the distribution of the defined regions of FIG. 6 are shown, and wherein each of the regions is filled according to a gray scale. The lightness of the gray scale indicates the local distortion factor for the image point associated with this region. For example, a darker grey indicates a region with a low local distortion factor, i.e. the state of the lacrimal layer is relatively good, while a lighter grey indicates a region with a high local distortion factor, i.e. the state of the lacrimal layer is relatively bad.

The map of FIG. 7 gives proper feedback to the operator of the device on the status of the lacrimal layer of the eye. This map may be displayed on a computer monitor or printed out.

The data of the map, or more generally the individual and/or combined local distortion factors may be stored in a database, for instance in the memory unit for future reference. The data may for example be used to monitor the state of the lacrimal layer in the course of time, for example to determine the time between blinking of an eye and tear film break up. But the data may also be used over a longer period of time, for example to determine the effects of treatment of ocular surface disorders, such as dry eye syndrome.

Figure 9:
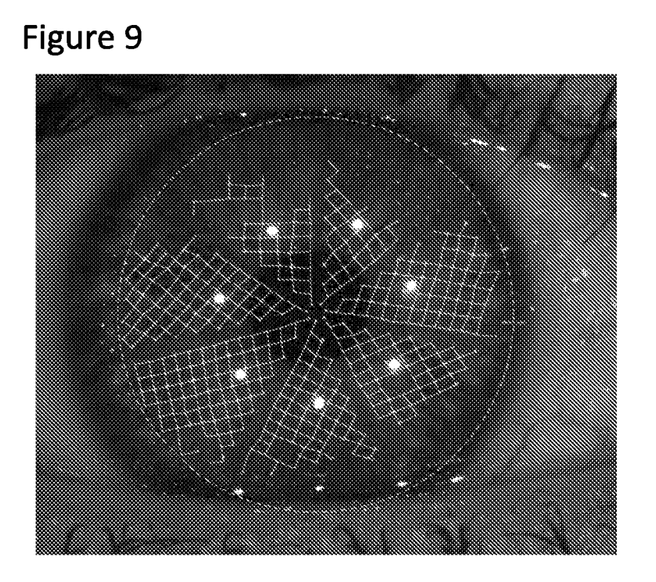

In FIGS. 9 and 10 another type of representations representative for the state of the lacrimal layer of a human eye is shown. This representation may for example be displayed by the display unit 181. The representation is based on gridlines drawn between centers of image points. When the source points would be perfectly reflected the gridlines would be straight lines that run parallel or perpendicular to each other. Non-straightness of the grid lines, or non-parallel or non-perpendicular gridlines indicate that there is distortion in the corresponding image points.

In an embodiment, the display device is arranged to display the data representative for the state of the lacrimal layer of the eye as a pattern of grid lines, wherein cross-points of the grid lines are formed by determine locations of the image points, and wherein the state of the lacrimal layer of the eye can be determined by the distortion within the pattern of grid lines.

FIG. 9 shows a grid line representation in which the grid lines are relatively straight and parallel or perpendicular. This indicates that the state of the lacrimal layer is relatively good.

FIG. 10 shows a grid line representation in which the grid lines are less straight and less parallel or perpendicular. This indicates that the state of the lacrimal layer is relatively bad.

Thus, the representations as shown in FIGS. 9 and 10, that are based on the comparison of the pattern of source points and the pattern of image points, provide data to the user representative for the state of the lacrimal layer of the eye, enabling the user to determine on the basis of the data the state of the lacrimal layer of the eye.

In another embodiment, the computational unit may be arranged to determine on the basis of the grid line representation the state of the lacrimal layer of the eye by analyzing the straightness of the grid lines and the parallelism or perpendicularity of the grid lines with respect to each other.

As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting, but rather, to provide an understandable description of the invention.

The terms "a" or "an", as used herein, are defined as one or more than one. The term plurality, as used herein, is defined as two or more than two. The term another, as used herein, is defined as at least a second or more. The terms including and/or having, as used herein, are defined as comprising (i.e., open language, not excluding other elements or steps). Any reference signs in the claims should not be construed as limiting the scope of the claims or the invention.

The mere fact that certain measures are recited in mutually different dependent claims does not indicate that a combination of these measures cannot be used to advantage.

A single processor or other unit may fulfil the functions of several items recited in the claims.

The invention claimed is:

1. A device to determine a state of the lacrimal layer of the eye, comprising: at least one light source arranged to form a pattern of source points for projecting a plurality of light rays onto a cornea surface; a lens-camera system arranged to receive a respective plurality of reflected light rays reflected on the cornea surface, thereby forming a pattern of image points; and a computational unit arranged to determine on the basis of the image points the state of the lacrimal layer of the eye and to determine on the basis of the image points data representative for the state of the lacrimal layer of the eye and to provide the data representative for the state of the lacrimal layer of the eye to a user.

2. The device of claim 1, wherein the computational unit is arranged to determine the state of the lacrimal layer of the eye on the basis comparing the source points and the image points and/or comparing the pattern of the source points and the pattern of the image points.

3. The device of claim 1, wherein the computational unit is arranged to determine for each of multiple image points, a value representative for local distortion of the respective image point, wherein the value representative for local distortion of the respective image point can be used to determine the state of the lacrimal layer of the eye.

4. The device of claim 3, wherein the computational unit is arranged to establish the value representative for local distortion of the respective image point by the following steps:
  defining regions around a central position of each image point, wherein the defined regions are non-overlapping and preferably adjacent;

analyzing the shape of each individual image point within its defined region; and quantifying the value representative for local distortion of the respective image point for each individual image point based on the analyzed shape.

5. The device of claim 1, wherein the computational unit is arranged to determine a pattern of grid lines, wherein cross-points of the grid lines are formed by determined locations of the image points, and wherein the state of the lacrimal layer of the eye, or data representative thereof, can be determined by a distortion within the pattern of grid lines.

6. The device of claim 1, wherein the device comprises a display device arranged to display the state of the lacrimal layer of the eye and/or the data representative for the state of the lacrimal layer of the eye.

7. The device of claim 1, wherein the computational unit comprises a memory unit provided with pattern information based on the pattern of source points, wherein the computational unit is arranged to, for each of the plurality of reflected light rays, establish a one-to-one correspondence between a source point and an image point based on the pattern information, and wherein the computational unit further is arranged to determine on the basis of a comparison of the image points and the source points the state of the lacrimal layer of the eye.

8. The device of claim 7, wherein the computational unit is arranged to determine the state of the lacrimal layer of the eye on the basis of individual comparisons of an image point of the pattern of image points and a corresponding source point of the pattern of source points.

9. The device of claim 1, wherein the computational unit is arranged to determine a value representative for global distortion of an image point, and wherein the value representative for global distortion of the respective image point is representative for effects of a global cause that affects a large number, possible all image points, in substantially the same way.

10. The device of claim 1, wherein the at least one light source comprises light sources that project light rays with different colours such that the pattern of source points comprises at least two different colors.

11. A method of determining a state of the lacrimal layer of an eye, the method comprising: projecting, with at least one light source, a plurality of light rays from a pattern of source points onto a cornea surface; receiving, a lens-camera system, a respective plurality of reflected light rays reflected on the cornea surface thereby forming a pattern of image points; and determining, with a computational unit, the state of the lacrimal layer of the eye on the basis of the image points and determining, with a computational unit, on the basis of the image points data representative for the state of the lacrimal layer of the eye and providing the data representative for the state of the lacrimal layer of the eye to a user.

12. The method of claim 11, wherein the step of determining the state of the lacrimal layer of the eye comprises comparing the source points and the image points and/or comparing the pattern of the source points and the pattern of the image points.

13. The method of claim 11, wherein the step of determining the state of the lacrimal layer of the eye comprises determining for each of multiple image points a value representative for local distortion of the respective image point, and wherein the value representative for local distortion of the respective image point can be used to determine the state of the lacrimal layer of the eye.

14. The method of claim 13, wherein the step of determining the value representative for local distortion comprises:

defining regions around a central position of each image point, wherein the defined regions are non-overlapping and preferably adjacent;

analyzing the shape of each individual image point within its defined region; and quantifying a value of the local distortion factor for each individual image point based on the analyzed shape.

15. The method of claim 11, wherein the method comprises the step of determining a pattern of grid lines, wherein cross-points of the grid lines are formed by determined locations of the image points, and wherein the distortion within the pattern of grid lines is representative for the state of the lacrimal layer of the eye.

16. The method of claim 11, wherein the method comprises displaying, with a display device, the state of the lacrimal layer of the eye and/or the data representative for the state of the lacrimal layer of the eye.

17. The method of claim 11, wherein the method comprises the steps of creating a map showing the local distortion of the respective image points or groups of image points.

18. The method of claim 11, the method further comprising:

providing pattern information based on the pattern of source points;

establishing a one-to-one correspondence between each of the source points and the respective image points based on the pattern information; and comparing the image points and the source points to determine the state of the lacrimal layer of the eye.

19. The method of claim 18, wherein the step of comparing comprises determining the state of the lacrimal layer of the eye on the basis of individual comparisons of an image point of the pattern of image points and a corresponding source point of the pattern of source points.

20. The method of claim 11, wherein the method comprises the steps of:

determining a value representative for global distortion of an image point, wherein the value representative for global distortion of the respective image point is representative for effects of a global cause that affects a large number, possible all image points, in substantially the same way, and correcting or compensating an individual image point for the effects of the global cause using the value representative for global distortion of the image point, and/or when the value representative for global distortion exceeds a predetermined threshold value determining that the pattern of image points is not suitable to determine the state of the lacrimal layer of the eye.

* * * * *